US006709270B2

United States Patent
Honkura et al.

(10) Patent No.: US 6,709,270 B2
(45) Date of Patent: Mar. 23, 2004

(54) DENTAL MAGNETIC ATTACHMENT

(75) Inventors: Yoshinobu Honkura, Aichi (JP); Kazuo Arai, Aichi (JP); Yasuhiro Takeuchi, Aichi (JP)

(73) Assignee: Aichi Steel Corporation, Tokai (JP)

( * ) Notice: Subject to any disclaimer, the term of this patent is extended or adjusted under 35 U.S.C. 154(b) by 0 days.

(21) Appl. No.: 10/162,583

(22) Filed: Jun. 6, 2002

(65) Prior Publication Data

US 2003/0124491 A1 Jul. 3, 2003

(30) Foreign Application Priority Data

Dec. 27, 2001 (JP) ........................................ 2001-397718

(51) Int. Cl.$^7$ ................................................ A61C 8/00
(52) U.S. Cl. ........................................ 433/174; 433/189
(58) Field of Search ................................. 433/173, 174, 433/189

(56) References Cited

U.S. PATENT DOCUMENTS

| 4,209,905 | A | * | 7/1980  | Gillings ........................ 433/189 |
| 4,215,986 | A |   | 8/1980  | Riess |
| 4,693,686 | A | * | 9/1987  | Sendax ........................ 433/173 |
| 4,997,372 | A | * | 3/1991  | Shiner et al. ................. 433/189 |
| 5,368,483 | A | * | 11/1994 | Sutter et al. .................. 433/173 |
| 5,376,004 | A | * | 12/1994 | Mena ........................... 433/173 |
| 5,421,722 | A |   | 6/1995  | Stemmann |
| 5,425,763 | A | * | 6/1995  | Stemmann .................... 623/11 |
| 5,447,434 | A |   | 9/1995  | Shaw |
| 5,458,488 | A |   | 10/1995 | Chalifoux |
| 5,611,689 | A | * | 3/1997  | Stemmann ..................... 433/189 |
| 5,915,967 | A |   | 6/1999  | Clokie |
| 5,954,506 | A | * | 9/1999  | Tanaka ......................... 433/214 |
| 6,302,694 | B1| * | 10/2001 | Honkura et al. ............... 433/189 |
| 6,540,515 | B1| * | 4/2003  | Tanaka ......................... 433/189 |

FOREIGN PATENT DOCUMENTS

| JP | 9-224959    | 9/1997 |
| JP | 2000-24004  | 1/2000 |
| JP | 2001-514924 | 9/2001 |
| WO | WO 99/08620 | 2/1999 |

OTHER PUBLICATIONS

Konux–Titanmagnetics (Komafix)—Ein Neues Verankerungselement Fuerdie Hybridprothetik, Kurt Jaeger et al., pp 75–80, 1998 (w/english abstract).

U.S. patent application Ser. No. 10/162,583, Honkura et al., filed Jun. 6, 2002.

U.S. patent application Ser. No. 10/394,226, Honkura et al., filed Mar. 24, 2003.

\* cited by examiner

*Primary Examiner*—Ralph A. Lewis
(74) *Attorney, Agent, or Firm*—Oblon, Spivak, McClelland, Maier & Neustadt, P.C.

(57) ABSTRACT

A dental attachment is disclosed which provides an improved connection force and fitting between an implant and a keeper. A keeper has a main body with a attracted face, a screw part that is located at the back face, a conical tapered shaft, and a projecting ring part. The projecting ring part has an inclining inner face and an acute angle pointed end. An implant has a screw hole part, a conical tapered hole part which has about the same inclining angle of the tapered axle part, and an inclining end face. When the keeper and the implant are connected, the tapered shaft and the tapered hole part are fitted closely and at the same time, the inner face of the acute angle pointed end and the inclining end part are in contact and at least the acute angle pointed end of the projecting ring part is elastically transformed toward the diameter.

3 Claims, 6 Drawing Sheets

DENTAL MAGNETIC ATTACHMENT

BACKGROUND OF THE INVENTION

1. Field of the Art

The present invention relates to a dental attachment that can be used to fix a denture to a dental implant keeper by the use of a magnetic force.

2. Prior Art

Various dental attachments using magnetic attractive force have been proposed in dental treatments, because it is a simple method to take off and fix the denture.

For example, the dental attachment 9 shown in Japanese Laid-Open Patent Number 9-224959, as shown FIG. 6, consists of an implant 91 acting as an abutment embedded in the jawbone, a keeper 93 fixed to this implant, and a magnetic assembly 95 which has an attractive surface 950 that attracts the attracted surface 930 of the keeper 93 by a magnetic attractive force.

The keeper 93 is fixed to said implant 91 by screwing screw part 931 of keeper 93 into screw hole 911 of implant 91. With this, the contact faces 912 and 932 fit together precisely and prevent alien substances from entering between implant 91 and keeper 93.

However maintenance of a fixing force solely by screwing the screw part 921 to screw hole 911 is not enough, and looseness may be caused during use of said dental attachment. This looseness may cause a sudden deterioration of fixation and cleanliness.

Therefore the development of a dental attachment that can maintain said fixation and stability between a keeper and an implant by the way of a screw is desired.

Taking into consideration the abovementioned requirements, the present invention provides a dental attachment that can improve the fixation and stability between an implant and a keeper.

SUMMARY OF THE INVENTION

The present invention is directed to a dental attachment which comprises an implant embedded in a jawbone, a keeper supported by said implant, and a magnetic assembly that has a attractive face that attracts an attracted face of said keeper by a magnetic attractive force.

The keeper has a main body that has said attracted face, a screw part that is located at the center of a back face which is opposite to said attracted face of said main body, a conically tapered shaft at the base end of said screw part, and a projecting ring part that projects toward the shaft to form a ring-shaped groove with said tapered shaft along the circumference of said back face.

Said projecting ring part has a slanted inner face that tapers toward a pointed end, and an acute angle pointed end that actually looks like an acute angled shape that intersects the outer face.

Said implant has a screw hole part into which said screw part of said keeper can be screwed, a conical tapered hole part which extends upward from the open side of said screw hole part and has approximately the same incline angle of said tapered shaft, and an inclining end face which slants upwards to the circumference of the opening of the tip of the implant.

The dental attachment has the feature such that when said keeper and said implant are screwed together, there is close contact of said screw part to said screw hole part, said tapered shaft to said tapered hole part, said inner face of said acute angle pointed end of said projecting ring part and said inclining end face of said implant, and at least said acute angled pointed end of said projecting ring part is elastically transformed in a radial direction.

The presently invented dental attachment has, as explained above, said tapered shaft of said keeper and an acute angled pointed end of said projecting ring part, while said implant has said tapered hole and said inclining end face. When a keeper is connected to an implant, as explained above, said tapered shaft is closely fitted to said tapered hole, and at the same time, said inner face of said acute angled pointing end and said inclined end face come into contact, and at least said acute angled pointed end of said projecting ring part is elastic transformed in a radial direction.

In this manner way, the connecting force between said keeper and implant is maintained by both the frictional force between said tapered shaft and tapered hole and the frictional force between said acute angled pointed end and said inclined end face. In particular, the frictional force between said tapered shaft and tapered hole part gives a much greater connecting force preventing loosening of the screw.

By the contact of said acute angled pointed end of said projecting ring part and said inclining end face, a precise fit can be made.

Even excellent parts processing in the prior art has had difficulty to achieve the accuracy of dimensions to adequately screw said tapered shaft to said tapered hole part and at the same time make said acute angled pointed end of said projecting ring part touch said inclining end face. But if said acute angled pointed end can be elastic transformed to some degree during screwing, adequate processing accuracy of a keeper and implant can be achieved, and in addition the two abovementioned places can be firmly fit together.

When connection is made in the abovementioned fashion where said acute angled end part is elastically transformed, said tapered shaft can be screwed into said tapered hole part and at the same time said acute angled pointed end of said projecting ring part can be connected to said inclining face without difficulty of said processing art. Thus both excellent prevention of screw loosening and prevention of filth intrusion can be achieved.

Therefore, according to the present invention, a dental attachment with an improved connection force and firm fitting between an implant and keeper can be achieved.

DESCRIPTION OF THE PREFERRED EMBODIMENT

In the present invention, it is preferred that at least said tapered shaft and the inner face of said acute angle pointed end of said keeper, and said tapered hole part and said inclining end face of said implant be surface-treated to enhance resistance to wear.

In this case, the length of wear of the dental attachment as a whole can be improved by the improvement of the resistance to wear of the connecting parts of said keeper and said implant.

In this case, a variety of usual surface treatments can be carried out to improve the resistance to wear, for example, coating of TiN, diamond, N, Cr, ceramics, nitrogen treatment, chrome treatment, etc.

It is preferred that a similar surface treatment is given to the attracted face of said keeper and the attractive face of said magnetic assembly. Thereby resistance to wear during fixing or removal of the denture can be improved.

It is also preferred that the outer face of said projecting ring part is like a cylinder that has no change of diameter. In this case, the outer face of said keeper is straight and generates no awkward feeling during use.

Said keeper is fixed on the implant (on the side towards the magnetic assembly), and makes a magnetic circuit with the magnetic assembly thus fixing a denture to an implant. The material of this keeper may be one of various anti-corrosive dental magnetic materials that have been used as keepers of dental magnetic attachments. In particular, it is preferred that magnetic materials be used which have greater than 1.3 T of saturation magnetic flux density and magnetic permeability greater than 3000. Such magnetic materials are iron-chrome-molybdenum alloy, and soft-magnetic stainless steel, such as 19Cr-2Mo-0.2Ti steel, 17Cr-2Mo-0.2Ti steel, etc.

Said magnetic assembly makes a magnetic circuit with a keeper and fixes a denture to an implant. This magnetic assembly comprises a magnet, and various magnets that have been used for dental magnetic attachments can be used. It is particularly desirable to use a magnet that has a high energy capacity. A magnetic material that has more than 2388 kJ/m energy capacity is desirable for practical use. Such magnetic materials are Nd—Fe—B type or Sm—Co type rare-earth magnets, etc.

Figure 1:
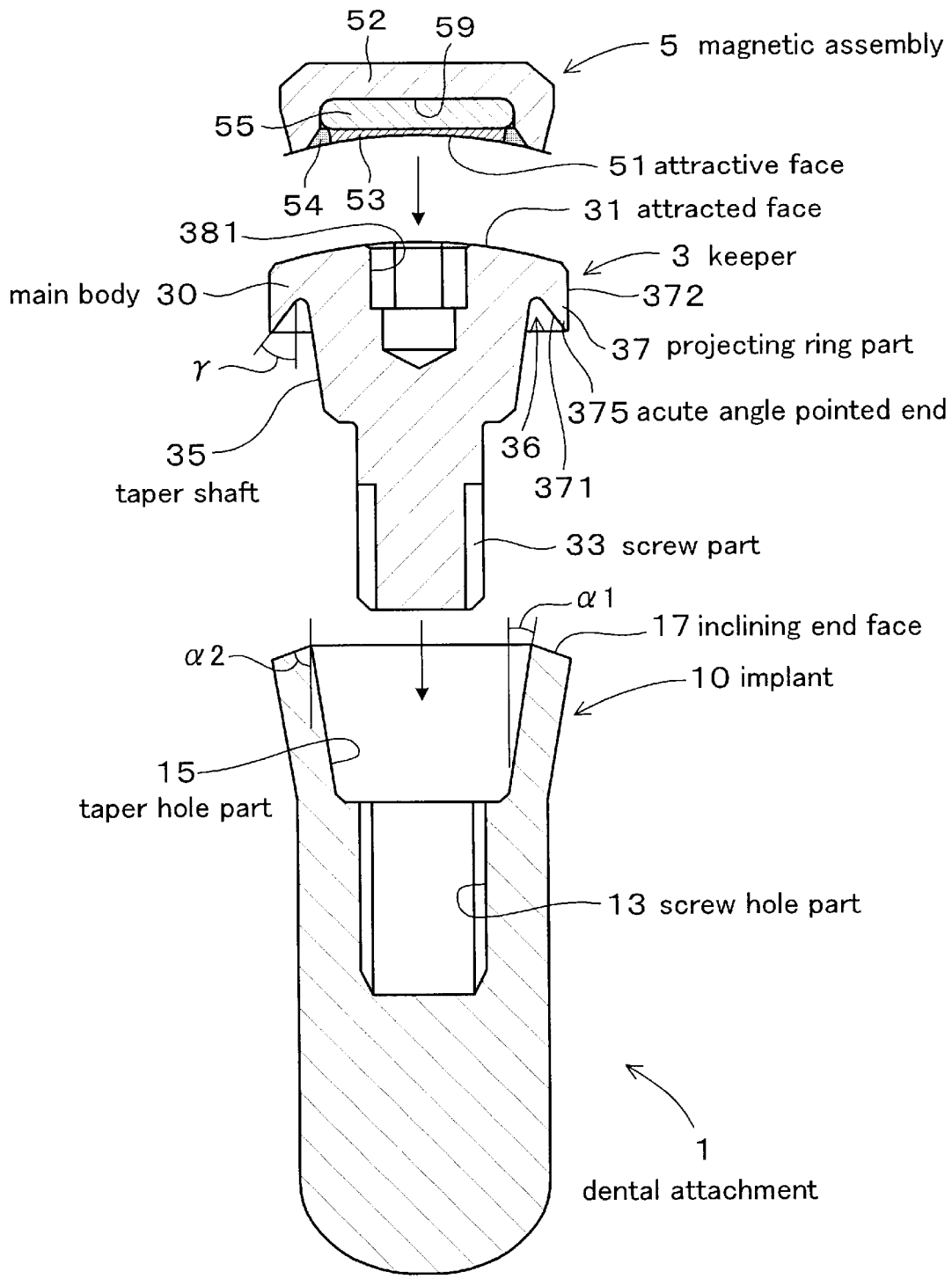
FIG. 1 is an illustration of the constitution of the dental attachment of Example 1.

The dental attachment 1 of this invention, as is shown in FIG. 1 as Example 1, comprises an implant 10 embedded in a jawbone, a keeper 3 supported by said implant 10, and a magnetic assembly 5 which has a contact face 51 to attract an attracted face 31 of said keeper 3 by a magnetic attractive force.

Said keeper 3 has a main body 30 that has attracted surface 31, screw part 33 that is located at the center of the back face opposite the attracted surface 31 of said main body 30, conic tapered shaft 35 at the base end of said screw part 33, and a projecting ring part 37 which projects toward the shaft to make a ring-shaped groove 36 with said tapered shaft 35 at the circumference of said back part.

Said projecting ring 37 has a slanted inner face 371 that tapers toward a pointed end and an acute angled pointed end 375 that actually has an acute angled-shape in appearance at the pointed part that intersects the circumferential face 372.

Said implant 10 has a screw hole part 13 into which said screw part 33 of said keeper 3 can be screwed, a conical tapered hole part 15 which is extends upward from the open side of said screw hole part 13 and has approximately the same inclined angle of said tapered shaft 35, and inclining end face 17 which slants upwards to the circumference of the opening of the tip of the implant.

In the case wherein said keeper 3 and said implant 10 are screwed together with said screw part 33 inserted in said screw hole part 13, said tapered shaft 35 and said tapered hole part 15 are closely fitted together, and inner face of said acute angled pointed end 375 and said inclining end face 17 touch each other and at least said acute angled pointed end 375 of said projecting ring part 37 is elastically transformed in the radial direction.

Said implant 10 is as shown in FIG. 1, and has a screw bulge on the side (the diagram is omitted). And at the top end, said screw hole part 13 and tapered hole part 15 are open.

In this example, the inclining angle α1 toward the shaft in said tapered hole part 15 is 8 degrees. The inclining angle α2 of inclining end face 17 in the open part toward the shaft is 48 degrees.

The implant 10 of this example is made of Ti.

Said keeper 3, as shown in FIG. 1, has an attracted face 31 of the main body 30 that has a convex dome shape whose radius of curvature is 8 mm. At the center of the attracted face 31, there is a hole to insert tool 318 (the diagram of which is omitted) which is used when a keeper 3 is screwed into the implant.

At the back face of the main body 30, a tapered shaft 35 is connected with a screw part 33 and said projecting ring part 37 is made to form a rounded groove 36 with tapered shaft 35.

In this example, the angle γ to the shaft of inner face 371 of projecting ring part 37 is 42 degrees and the outer face 372 is made straight like a cylinder that has no change of diameter.

The part between said inner face 371 and outer face 372 of said projecting ring part 37 is said acute angled pointed end 375 whose angle is 48 degrees. The top of the acute angled pointed end 375 is chamfered to some degree enough to provide durability and security.

Said keeper 3 is made of 19Cr-2Mo-0.2Ti. In this example, said tapered shaft 35, the inner face of said acute angled pointed end 375 (inner face 371), and attracted face 31 are surface-treated to enhance the resistance to wear. A coat of TiN is given by ion plating.

Said magnetic assembly 5, as shown in FIG. 1, comprises a magnet 55 that has N pole and S pole arranged perpendicular to the direction of tooth length, a first yoke 52 that has a concave part 59 into which said magnet 55 is inserted, a second yoke 53 that is placed over the open part of said first yoke and seals said magnet 55 and is opposite to a keeper 3, and a non-magnetic part 54 that is between said first yoke 52 and second yoke 53.

Said magnetic assembly 5 has a attractive face 51 which is formed by said first yoke 52, second yoke 53, and non-magnetic part 54 and which has a concave domed surface to fit attracted face 31 of said keeper 3. The radius of curvature of the concave domed surface of this example is 8 mm.

Also, the attractive face 51 of said magnetic assembly 5 is surface-treated by TiN coat to enhance the resistance to wear.

The magnetic assembly 5 is made of Nd type rare earth magnet. The first yoke 52 and the second yoke 53 are made of 19Cr-2Mo-0.2Ti magnetic stainless steel.

In the case that dental attachment 1 with said structure is used, first, said implant 10 is embedded in the jawbone (the diagram of which is omitted). Next, said keeper is screwed to the implant.

In this example, the dimensions of said keeper 3 and implant are formed by the following actions.

Figure 2:
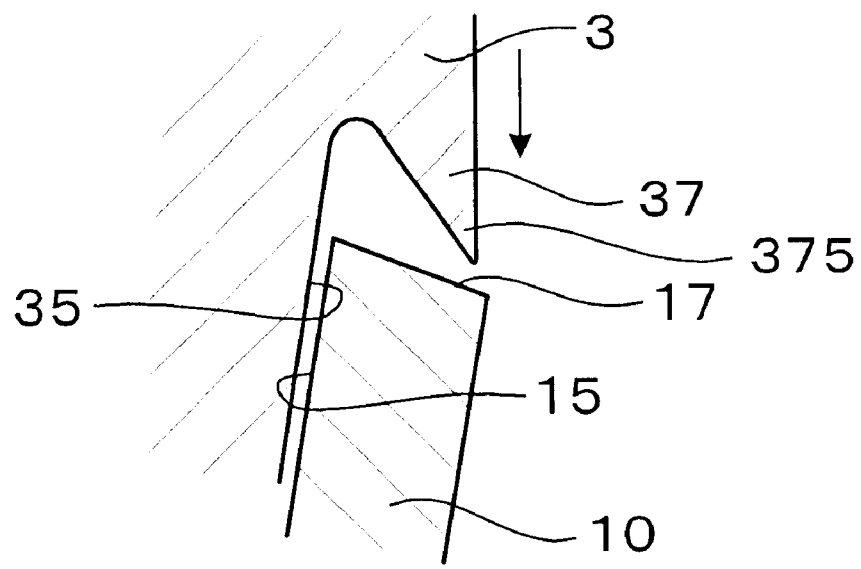
FIG. 2 is an illustration of an early stage of connection of a keeper and an implant.

That is, as is shown in FIG. 2, by screwing the screw part 33 of the keeper 3 into the screw hole 13 of the implant 10, the tapered shaft 35 and the acute angled pointed end 375 of the keeper 3 approach the tapered hole 15 and inclining end face 17.

Figure 3:
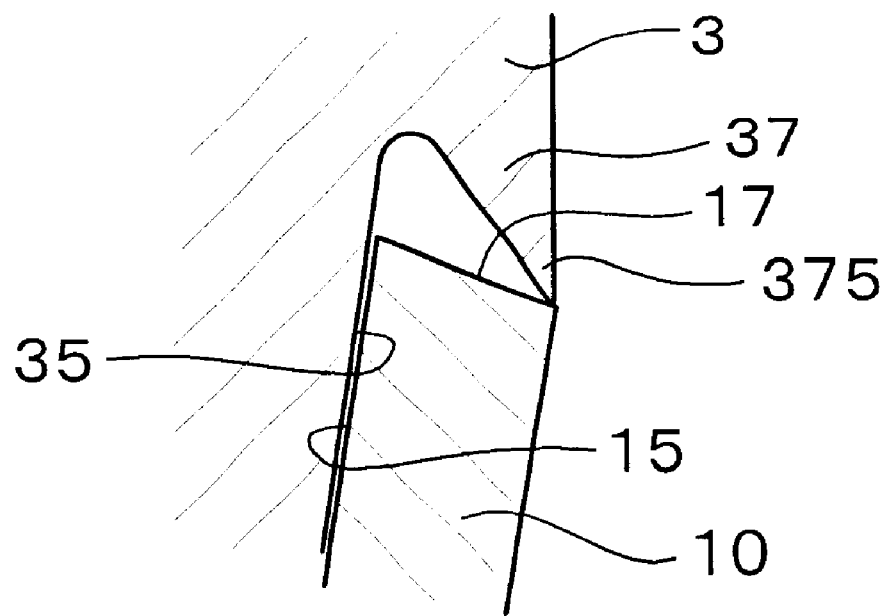
FIG. 3 is an illustration of the moment of connection between an acute angled pointed end and an inclining end face when a keeper is connected with an implant.

And, as is shown in FIG. 3, in the case that there is some space between tapered shaft 35 and tapered hole part 15 which can be closed by tightening, acute angled pointed end 375 touches inclining end face 17. Still it is not necessary to maintain an untouched condition, if there is still some margin to be tightened between tapered shaft 35 and tapered hole 15.

Figure 4:
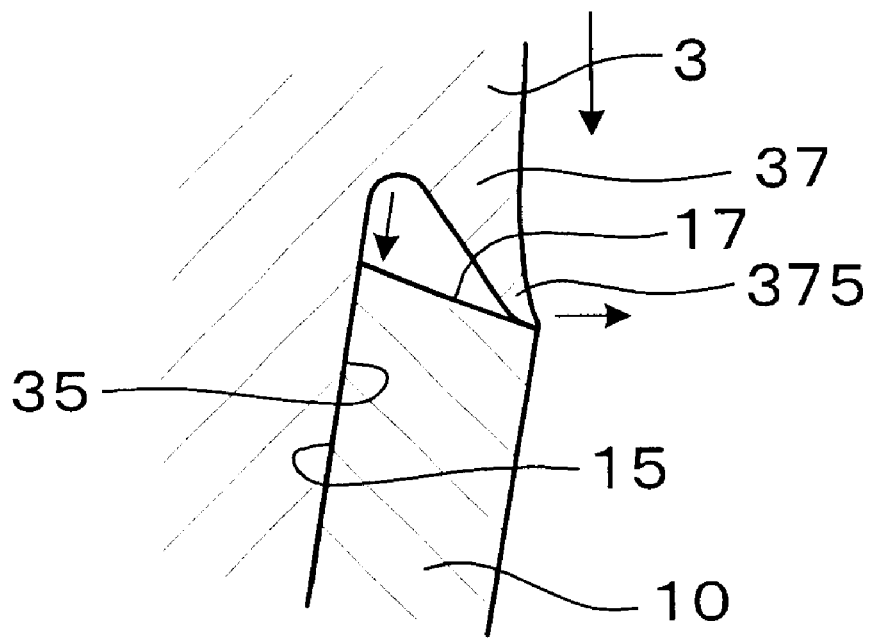
FIG. 4 is an illustration of the condition where a keeper has been connected to an implant in Example 1.

Next, as shown in FIG. 4, as keeper 3 is screwed, the stress in the outer direction is gradually transmitted to the acute angle pointed end 375 along said inclining end face 17 and in the condition that tapered shaft 35 and tapered hole part 15 are screwed together firmly, said acute angled pointed end 375 is elastically transformed in the radial direction.

Thereby, the connecting force between keeper 3 and implant 10 is made by both the frictional force between tapered shaft 35 and tapered hole part 15 and the frictional force between said acute pointed end 375 and inclining end face 17. Especially, the frictional force between tapered shaft 35 and tapered hole part 15 can give a significantly stronger connection force for prevention of screw loosening.

Thereby, in said connected condition, because said acute angled pointed end 375 is elastically transformed, both adequate connection between acute angled pointed end 375 of said projecting ring part 37 and inclining end face 17, and the adequate connection between said tapered hole part 15 and tapered shaft 35 can be achieved at the same time when screwing, and both excellent prevention of screw loosing and preventing of intrusion of filth can be achieved.

Figure 5:
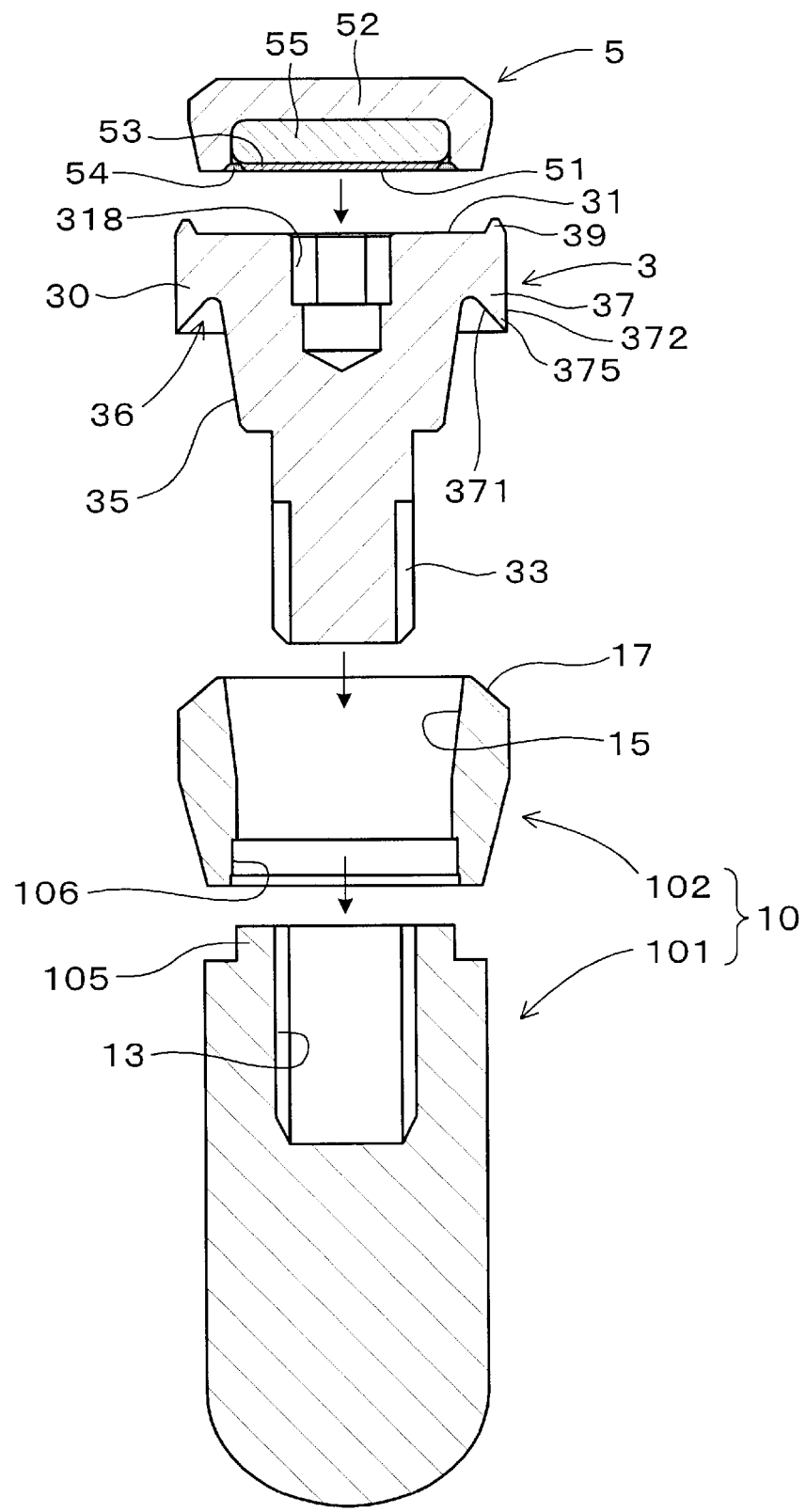
FIG. 5 is an illustration of the constitution of the dental attachment of Example 2.
Figure 6:
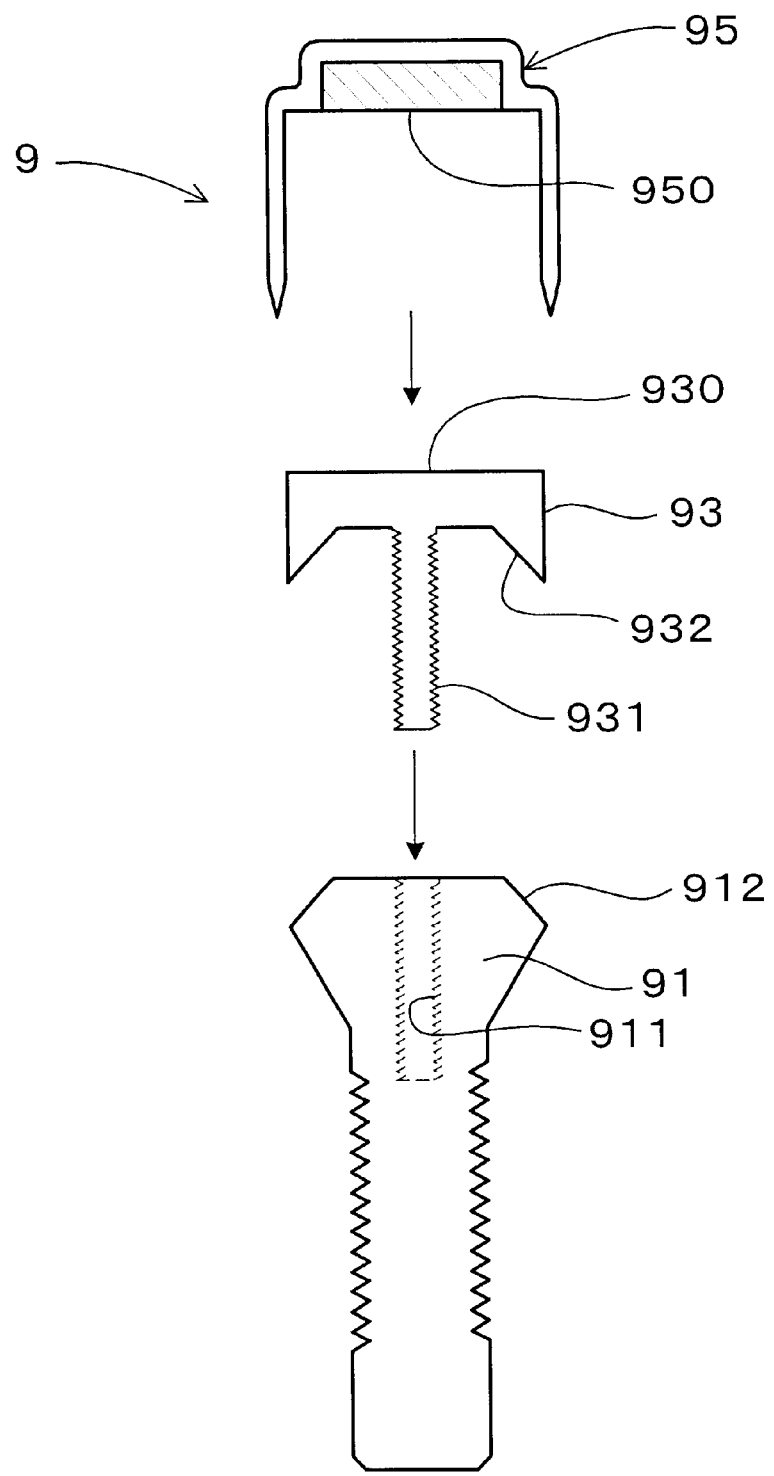
FIG. 6 is an illustration of the constitution of the dental attachment of the prior art example.

Example 2, as shown in FIG. 5, is comprised of an implant which has a little different constitution, a keeper 3, and a magnetic assembly 5.

Said implant 10, as shown in FIG. 5, is changed into a two-piece structure. Lower part 101 which has a screw hole part 13 and an upper part 102 which has tapered hole part 15 and an inclined inclining end face 17.

Also, said lower part has a hexagonal projecting part 105 on the top end and upper part 102 has a hexagonal concave part 106. By making the projecting part 105 fit to the concave part 106, the precise position of lower part 101 and upper part 102 is determined and rotation between the two pieces is stopped.

Said keeper 3 has, as is shown in FIG. 5, an attracted face 31 which is flat and has a ring-shaped control part 39 on the circumference. This control part controls the position of magnetic assembly 5. Said magnetic assembly 5 has an attractive face which is flat.

Other structures are substantially the same as the dental attachment 1 of Example 1. The shape and dimensions of the tapered shaft 35 and acute angle pointed end 375 of the keeper, and tapered hole part 15 and inclined end face 17 of implant 10 are the same as in example 1.

In the case of this example, as is in Example 1, when keeper 3 is connected to implant 10, said tapered shaft 35 is fitted to said tapered hole part 15 and the inner face of said acute angled pointed end 375 and said inclined end face 17 are in contact, and at least said acute angled pointed end 375 of said projecting ring part 37 is elastically transformed toward the diameter. Therefore, a very excellent connection force and fitting can be achieved.

What is claimed is:

1. The dental magnetic attachment comprising:

an implant adapted to be embedded in jawbone, a keeper supported by said implant and a magnetic assembly that has a surface which attracts a surface of said keeper by magnetic attractive force, said keeper having a body having said attracted surface, a screw part that is located at the center of the back face which is opposite said attracted surface of said body, a conical tapered shaft at the base of said screw part, and a projecting ring part which projects toward the shaft to form a ring-shaped groove with said tapered shaft at the outer part of said back part, said projecting ring part having a slanted inner face that tapers toward a pointed end, and an acute angle $\gamma$ at said pointed end, an abutment for fixing the keeper thereto which has a screw hole part into which said screw part of said keeper is screwed, a conical tapered hole part which extends upward from the open side of said screw hole part and has approximately the same inclined angle of inclination as said tapered shaft, and has an inclined end face which slants upwards to a circumference of the opening of the tip of the implant at an angle $\alpha 2$ wherein $\gamma < \alpha 2$, wherein when said keeper and said implant are connected by said screw part upon being screwed into said screw hole part, said tapered shaft and said tapered hole part are connected, and only a tip portion of said inner face of said acute angle pointed end and only a peripheral portion of said inclining end face are in contact, and at wherein least said acute angle pointed end of said projecting ring part is elastically transformed radially.

2. The dental attachment as set forth in claim 1, wherein at least said tapered shaft and said acute angle pointed end of said keeper, and said tapered hole part and said inclining end face of said implant are surface-treated to enhance resistance to wear.

3. The dental attachment as set forth in claim 1 or 2, wherein the outer face of said projecting ring part has a cylindrical shape that has no change in diameter.

* * * * *